United States Patent [19]
Bringhen et al.

[11] Patent Number: 6,048,516
[45] Date of Patent: Apr. 11, 2000

[54] LIGHT-SCREENING AGENTS

[75] Inventors: Alain Bringhen, Croix-de-Rozon; Hans Ulrich Gonzenbach; Magali Pochon, both of Geneva, all of Switzerland

[73] Assignee: Roche Vitamins Inc., Parsippany, N.J.

[21] Appl. No.: 09/113,863

[22] Filed: Jul. 10, 1998

[30] Foreign Application Priority Data

Jul. 14, 1997 [EP] European Pat. Off. ............... 97111938

[51] Int. Cl.⁷ ............................... A61K 7/42; A61K 7/00
[52] U.S. Cl. ..................... 424/59; 424/60; 424/400; 424/401
[58] Field of Search ................... 424/59, 60, 400, 424/401

[56] References Cited

U.S. PATENT DOCUMENTS

| | | | |
|---|---|---|---|
| 3,270,045 | 8/1966 | Strobel et al. | 424/59 |
| 3,275,520 | 9/1966 | Strobel et al. | 424/59 |
| 4,387,089 | 6/1983 | De Polo | 424/59 |

FOREIGN PATENT DOCUMENTS

| | | |
|---|---|---|
| 1221225 | 7/1966 | Denmark . |
| 1242780 | 6/1967 | Denmark . |
| 19540952 | 5/1997 | Denmark . |
| 709 080 | 4/1996 | European Pat. Off. . |
| 754 445 | 1/1997 | European Pat. Off. . |
| 780 119 | 6/1997 | European Pat. Off. . |
| WO 91/11989 | 8/1991 | WIPO . |
| WO 92/20690 | 11/1992 | WIPO . |
| WO 9717054 | 5/1997 | WIPO . |
| WO 97/21422 | 6/1997 | WIPO . |

OTHER PUBLICATIONS

Abstract corresponding to WO 91/11989.
Abstract corresponding to WO 97/21422.
SOFW Journal, 122, vol. 8 (1996) 543.
Cosmetics & Toiletries vol. 107 (1992) 45.
International Journal of Cosmetic Science vol. 18, pp. 167–177 (1996).
G. Charles, Bull. Soc. Chim. Fr. 1559 (1962).
P.L. Pickard & T.L. Tolbert, J. Org. Chem. vol. 26, (1961) 4886.
Abstract corresponding to DE 19540952 & WO 9717054 (B4 & B5).
Abstract corresponding to DE 1221225 (B7).
Abstract corresponding to DE 1242780 (B8).

*Primary Examiner*—Shelley A. Dodson
*Attorney, Agent, or Firm*—George W. Johnston; Dennis P. Tramaloni

[57] ABSTRACT

The invention relates to a composition which comprises a dibenzoylmethane capable of absorbing UV-A radiation and a compound of formula I

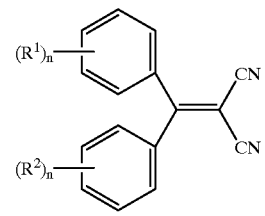

wherein $R^1$ and $R^2$ are independently hydrogen, alkyl or alkoxy containing 1 to 18 carbon atoms provided that $R^1$ and $R^2$ are not both hydrogen; and n is 1 or 2 in an amount effective to photostabilize the dibenzolymethane, and a cosmetically acceptable carrier, and to cosmetic light-screening compositions containing at least one of the above agents, the use of the cosmetic light-screening compositions for the protection of the human skin and human hair against the ultraviolet radiation of wavelengths between about 320 and 400 nm (UV-A) and optionally also between about 290 and 400 nm (UV-B).

40 Claims, 3 Drawing Sheets

LIGHT-SCREENING AGENTS

BACKGROUND OF THE INVENTION

Dibenzoylmethane compounds are known to absorb ultraviolet radiation in the 320 to 400 nm range (UV-A) and accordingly act as UV-A light screening agents. However, no UV-A blocking sunscreen can be used alone if absorbtion in a wide range of UV-radiation is required. Thus, UV-A filters usually must be combined with UV-B absorbing agents. Unfortunaltelly, when dibenzoylmethane compounds are used alone or in combination with UV-B screening agents, the dibenzoylmethane type UV-A screening agents are photolabile and it is necessary to photostabilize the dibenzoylmethane type UV-A filters.

Photostabilization in this context means to maintain a constant or nearly constant protection of human skin or hair by such a UV-A screening agent against ultraviolet light in the range of 320 to 400 nm.

Up to now, UV-A screening agents have been photostabilized by adding specific UV-B filter compounds known for this purpose. For example the UV-A screening agent 4-tert.butyl-4'-methoxydibenzoylmethane (U.S. Pat. No. 4,387,089) sold as PARSOL 1789® by F. Hoffmann-La Roche AG, is stabilized by Octocrylene (see EP-A-780 119), benzylidenes (see EP-A-754445), especially by methylbenzylidene camphor, or by a polymer of the benzylidene malonate silicone type (see EP-A-708080), which photostabilizing compounds are all UV-B filters.

The German patent publication DE 19540952 or the corresponding International publication WO 9717054 address to the problem of unsufficient photochemical stability of dibenzoylmethane type UV-A filters. It is suggested to use dicyanodiphenylethylene derivatives as UV-A filters instead of dibenzoylmethane type UV-A filters in cosmetics also containing compounds absorbing UV-B. The dicyanodiphenylethylene derivatives absorb in the 320–380 nm region and are stable to light. There is no teaching nor any guidance in the German patent publication DE 19540952 that would prompt the skilled person to use the well established photolabile dibenzoylmethane UV-A filter and to photostabilize it by adding dicyanodiphenylethylene derivatives.

SUMMARY OF THE INVENTION

Surprisingly it has now been found that dicyanodiphenylethylene derivatives of formula I

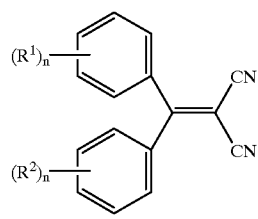

I where $R^1$ and $R^2$ are independently hydrogen, alkyl or alkoxy containing 1 to 18 carbon atoms provided that $R^1$ and $R^2$ are not both hydrogen; and n is 1 or 2, are capable of photostabilizing dibenzoylmethane type UV-A screening agents.

Accordingly, this invention is directed to a composition which comprises a dibenzoylmethane capable of absorbing UV-A radiation and a compound of formula I

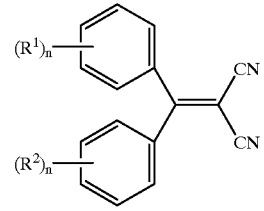

I wherein $R^1$ and $R^2$ are independently hydrogen, alkyl or alkoxy containing 1 to 18 carbon atoms, provided that $R^1$ and $R^2$ are not both hydrogen; and n is 1 or 2 in an amount effective to photostabilize the dibenzolymethane, and a cosmetically acceptable carrier.

Compositions of this invention are effective to guarantee constant protection during prolonged exposure to the UV light. This way, if a repeated application at various intervals is required, these intervals can be extended since the UV-A screening function of the dibenzoylmethane has been stabilized against undesired photochemical reactions and therefore lasts longer.

A UV-B screening agent or filter (i.e. a compound which absorbs radiation in the UV-B range of about 290 to 320 nm) may be part of these compositions. In this regard, since the compositions are stabilized with a compound of formula I, it is not necessary to be limited to one of the few particular UV-B screening agents capable of photostabilizing dibenzoylmethane. Any UV-B screening agent may be selected based on its suitability with regard to desirable properties, for example as a cosmetic. For example UV-B-filters are conveniently selected according to the desired chemical and physical properties of the formulation, e.g. according to the desired degree of protection, to wavelength, $e_{max}$, solubility, photostability, safety, see e.g. SÖFW (Journal) 122, 8 (1996) 543 seq., Cosmetics & Toiletries 107 (1992) 45 seq.

A BRIEF DESCRIPTION OF THE FIGURES

FIG. 1: Irradiation data showing percent area of 2% Parsol 1789 mixture remaining after exposure to UV-A radiation. A1, A2, A3: Parsol 1789 mixed with 1% of a compound of formula I; A4: Parsol 1789 alone; A5, A6: Parsol 1789 mixed with 1% benzophenone and 1% octocrylene, respectively.

FIG. 2: Irradiation data showing percent area of 2% Parsol 1789 mixture remaining after exposure to UV-A radiation. B1, B2, B3: Parsol 1789 mixed with 2% of a compound of formula I; B4: Parsol 1789 alone; B5, B6: Parsol 1789 mixed with 2% benzophenone and 2% octocrylene, respectively.

FIG. 3: Irradiation data showing percent area of 2% Parsol 1789 emulsion remaining after exposure to simulated sunlight radiation. C1, C2: Parsol 1789 with a compound of formula I; C3: Parsol 1789 alone; C4, C5: Parsol 1789 with benzophenone and octocrylene, respectively. See Table 4 for remaining ingredients.

DETAILED DESCRIPTION OF THE INVENTION

Figure 1:
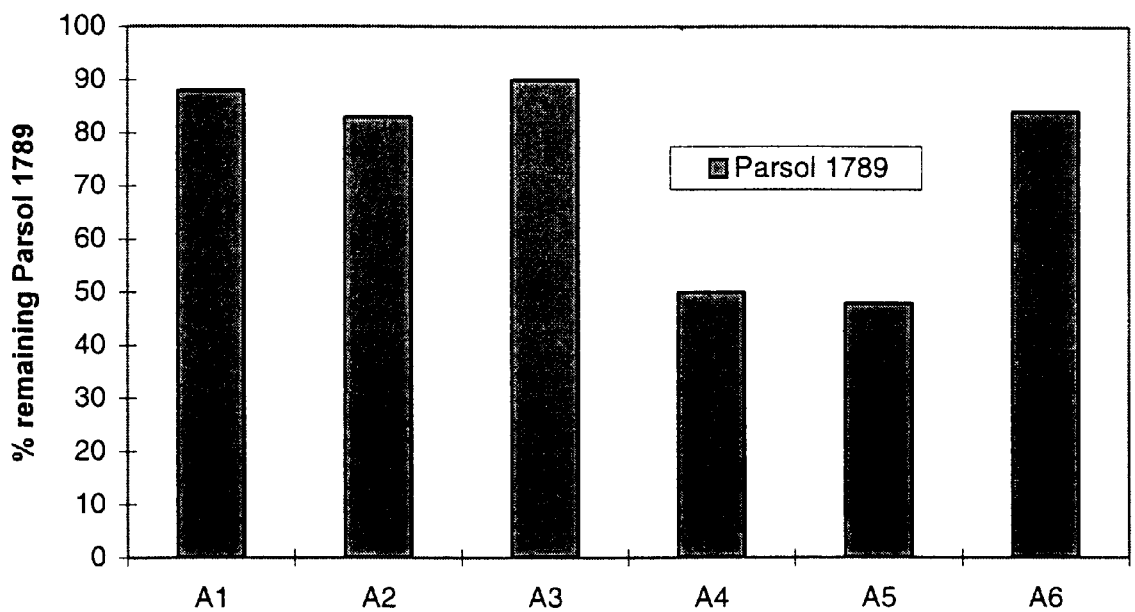

The compositions of this invention comprise dibenzoylmethane capable of absorbing UV-A radiation and a compound of formula I

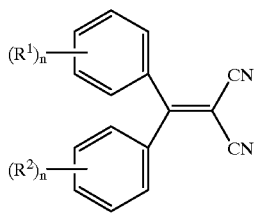

wherein $R^1$ and $R^2$ are independently hydrogen, alkyl or alkoxy containing 1 to 18 carbon atoms provided that $R^1$ and $R^2$ are not both hydrogen; and n is 1 or 2 in an amount effective to photostabilize the dibenzolymethane, and a cosmetically acceptable carrier. Preferably the alkyl or alkoxy contains 3 to 12 carbon atoms. Compositions of this invention may include one or more different dibenzoyl-methanes and one or more different compounds of formula I.

Alkyl and alkoxy in this invention are substituent groups (radicals) which are linear (for example $CH_3CH_2CH_2CH_2-$, $CH_3CH_2CH_2CH_2CH_2CH_2CH_2O-$) or branched at one, or more, sites (for example $CH_3CH(CH_3)CH_2CH2-$, $CH_3CH(CH_2CH_3)CH_2CH_2CH_2CH_2CH(CH_3)CH_2CH_2O-$), and contain a total of eighteen (18) carbon atoms, including carbons in the "branch" if present. Similarly, lower alkyl or alkoxy are branched or linear and contain a total of one to five carbon atoms.

The present invention thus relates to photostable dibenzoylmethane type UV-A screening agents stabilized by at least one compound of formula I

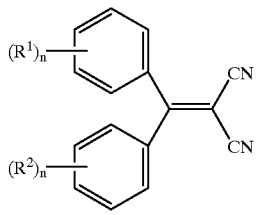

wherein $R^1$ and $R^2$ are equal or different and represent linear or branched alkyl or alkoxy radicals with 1 to 18 C atoms or one of $R^1$ and $R^2$ is a hydrogen atom and n is 1 or 2. Specifically, $R^1$ and $R^2$ are alkoxy radicals with 3 to 12 C atoms or one of $R^1$ and $R^2$ may be a hydrogen atom whereby $R^1$ and/or $R^2$ are/is in para configuration and n is 1. The alkoxy radical may especially be one of the group consisting of n-propoxy-, isopropoxy-, n-butoxy-, 1-methylpropoxy-, 2-methylpropoxy-, n-pentoxy-, 1,1-dimethylpropoxy-, 3-methylbutoxy, hexoxy-, 2,2-dimethylpropoxy-, heptoxy-, 1-methyl-1-ethylpropoxy, 2-ethylhexoxy- and octoxy-. The alkyl radical may be one of the group consisting of propyl, isopropyl, n-butyl, tert.butyl, pentyl, hexyl, preferably tert.butyl.

In this respect compounds of formula I wherein $R^1$ and $R^2$ are alkoxy radicals, especially branched alkoxy radicals, with 3 to 12 carbon atoms or one of $R^1$ and $R^2$ is a hydrogen atom where $R^1$ and/or $R^2$ are/is in para-configuration and n is 1 and where an alkoxy radical from the group consisting of n-propoxy-, isopropoxy-, n-butoxy-, 1-methylpropoxy-, 2-methylpropoxy-, n-pentoxy-, 1,1-dimethylpropoxy-, 3-methylbutoxy-, hexyoxy-, 2,2-dimethylpropoxy-, heptoxy-, 1-methyl-1-ethylpropoxy-, 2-ethylhexoxy- and/or octoxy-, are of specific interest.

A preferred compound of formula I for use in the claimed composition is the compound of formula I wherein $R^1$ is an hydrogen atom and $R^2$ is $H_9C_4O-$ (especially butoxy). Other suitable compounds of this particular type are: compounds of formula I wherein $R^1$ and $R^2$ are both 2-ethylhexoxy and compound of formula I wherein $R^1$ is an hydrogen and $R^2$ is a tert.butyl.

A compound of formula I in the composition of this invention has at least one ring which is substituted at any position with an alkyl or alkoxy group as described above. A preferred position on either or both rings is the para position. Either or both rings may be substituted at one position (for n is 1) or at two positions with identical substituents (for n is 2). Thus if $R_1$ were methyl and $R_2$ were ethoxy and n were 2, then one ring would have two methyl substituents and the other ring would have two ethoxy substituents. It is not necessary that both $R^1$ and $R^2$ be alkyl or alkoxy when n is 2, either one can be hydrogen.

For purposes of this invention, though either $R^1$ or $R^2$ can be hydrogen in a compound of formula I, by convention $R^1$ will be assigned the hydrogen and $R^2$ will represent the alkyl or alkoxy substituent as described above. Since such a compound is symmetric, any such compound where $R^1$ is hydrogen and $R^2$ is a substituent also describes the same compound where $R^2$ is hydrogen and $R^1$ is the substituent. For example, a compound where $R^1$ is hydrogen and $R^2$ is tert.butyl covers a compound where $R^1$ is tert.butyl and $R^2$ is hydrogen.

Compositions of this invention include the compound of formula I in several preferred embodiments. In one such embodiment, n is 1. In addition, $R^1$ may be hydrogen. In such a compound, $R^2$ is preferably in the para position, especially where n is 1 and $R^1$ is hydrogen.

In a preferred compound of formula I, $R^1$ and $R^2$ are alkyl or alkoxy containing 3 to 12 carbon atoms, and n may be 1 in addition. Also, either or both of $R^1$ and $R^2$ are in the para position. In preferred compounds, $R^1$ and $R^2$ are alkoxy containing 3 to 12 carbon atoms, especially n-propoxy-, isopropoxy-, n-butoxy-, 1-methyl propoxy-, 2-methylpropoxy-, n-pentoxy-, 1,1-dimethylpropoxy-, 3-methylbutoxy-, hexoxy-, 2,2-dimethylpropoxy-, heptoxy-, 1-methyl-1-ethylpropoxy-, 2-ethylhexoxy- and octoxy, and in particular 2-ethylhexoxy. In any of these compounds either or both of $R^1$ and $R^2$ may be in the para position.

In another preferred compound of formula I where n is 1 and $R^1$ is hydrogen, $R^2$ is alkyl or alkoxy containing 3 to 12 carbon atoms. In one such compound, $R^2$ is alkyl. Preferred are tert.butyl, propyl, isopropyl, n-butyl, pentyl, and hexyl, especially tert.butyl. In any of these compounds (in particular the former), $R^2$ may be in the para position. In another such compound, $R^2$ is alkoxy. Preferred are n-propoxy-, isopropoxy-, n-butoxy-, 1-methyl propoxy-, 2-methylpropoxy-, n-pentoxy-, 1,1-dimethylpropoxy-, 3-methylbutoxy-, hexoxy-, 2,2-dimethylpropoxy-, heptoxy-, 1-methyl-1-ethylpropoxy-, 2-ethylhexoxy- and octoxy, especially n-butoxy. In any of these compounds (in particular the former), $R^2$ may be in the para position.

For purposes of this invention, dibenzolymethane as used here includes both unsubstituted and substituted dibenzoyl-methanes which are capable of absorbing UV-A radiation, e.g. radiation of about 320 to about 400 nm. Compounds which absorb UV radiation are UV filters or screening agents, and can be used to protect skin, hair, or other compounds from the effects of UV radiation.

Compositions of this invention include dibenzoyl-methanes with one or more (linear or branched) lower alkyl or lower alkoxy groups, preferably methyl, tert-butyl, isopropyl, or methoxy. Preferred substitution positions are positions 2, 4, 5, 6, and 4'. One or more group may be substituted, for example at 2 and 4 or 2, 6, and 4'. These groups may be the same or different. Especially preferred dibenzoylmethanes are 2-methyldibenzoylmethane, 4-methyl-dibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane. Most preferred is 4-tert-butyl-4'-methoxydibenzoylmethane (Parsol 1789®, U.S. Pat. No. 4,387,089 or CH Pat. No. 642 536).

Any composition of this invention may additionally comprise one or more compounds capable of absorbing UV-B radiation. As defined above, compounds which absorb UV radiation are UV filters or screening agents, and can be used to protect skin, hair, or other compounds from the effects of UV radiation.

Preferred compounds capable of absorbing UV-B radiation are known ones, e.g. as inter alia described in U.S. Pat. No. 4,387,089 or in the patent publication DE 195 40 952 mentioned above. Preferably, the UV-B filter agents are cinnamates, salicylates, benzophenones, diphenylacrylates, camphor derivates, polymeric materials and microfine pigments having a particle size in the nano- and/or low micrometer region. More preferably the UV-B filter agents are pigment metallic oxides of cerium, iron, titanium, zinc or zirconium, especially of titanium or zinc, and polymers with hydrocarbon structure or siloxane structure i.e. polysiloxanes carrying at least one ultraviolet-light-absorbing group. Suitable polysiloxanes are disclosed in the above mentioned EP-A-754445 or in WO 92/20690.

Any composition of this invention includes a compound of formula I and a dibenzoylmethane, and may in addition include a compound capable of absorbing UV-B radiation. In preferred compositions, the dibenzolymethane is 4-tert-butyl-4'-methoxydibenzoylmethane, and the compound of formula I is a compound where n is 1 and $R^1$ is hydrogen and $R^2$ is tert.butyl or n-butoxy, preferably in the para position, or where $R^1$ and $R^2$ are both 2-ethylhexoxy, preferably both in the para position. These compositions are especially preferred when said compound of formula I is about 0.1% to about 5.0%, and preferably about 0.5% to about 2.0% by weight of the composition. These are especially preferred compositions, however in general a composition of this invention may be obtained using any compound of formula I described herein, in combination with any of the dibenzoylmethanes described herein, and optionally any of the UV-B filter compounds also described herein. A composition of this invention may include more than one of any of these component compounds.

The compound of formula I is present in an amount sufficient to photostabilize the dibenzoylmethane (that is to prevent the dibenzoylmethane from being broken down/decomposed by exposure to UV light over time). This amount is readily arrived at by a skilled person using standard assays for determining whether a compound is photostable. An example of such an assay is provided below. Briefly, an amount of dibenzoylmethane is combined with a compound of formula I, spread onto a surface in a predetermined area, and irradiated with UV-A light, which will break down the dibenzoylmethane so that it is no longer detectable on the surface in that form. The surface is then immersed in a solvent and HPLC is performed to determine the amount remaining of nondecomposed dibenzoylmethane. In more detail, the desired stabilization of the material of UV-A filters is easily established by strictly parallel experiments with the respective UV-A filters and the compounds of formula I using an appropriately equipped Xenon lamp as a solar simulator. The method is described in International Journal of Cosmetic Science 18, 167–177 (1996). Irradiated are standard preparations of the investigated products, e.g. solutions in, preferably, higher boiling cosmetic solvents, e.g. isopropyl myristate, the resulting sunscreen being spread on glass plates. After the irradiation, the plates are immersed into a suitable solvent (e.g. ethanol) and analysed by HPLC. The stabilising effect is directly correlated to the difference in area before and after the irradiation. Usually, a combination of UV-A filter and stabiliser as exemplified below is used for the assessment. Compounds of formula I wherein $R^1$ is a hydrogen atom and $R^2$ is $H_9C_4O$— (for example n-butoxy) or wherein $R^1$ and $R^2$ are both 2-ethylhexoxy or wherein $R^1$ is hydrogen and $R^2$ is a tert.butyl were found to be very efficient in photostabilizing a dibenzoylmethane screening agent of UV-A type, especially in photostabilizing 4-tert.butyl-4'-methoxybenzoylmethane.

An effective amount of compound of formula I is that amount which when mixed with a given amount of dibenzoylmethane, reduces the extent of its decomposition on exposure to UV-A light as determined by an assay such as that provided above and in the Examples. However, preferred stabilizing amounts of the compound of formula I are about 0.1 to about 5.0% by weight of the composition, especially about 0.5 to about 2.0% by weight of the composition. Thus a preferred composition of this invention comprises about 0.1 to 5.0% by weight, especially about 0.5 to about 2.0 by weight of a compound of formula I. Any compound of formula I mentioned in this invention is preferably present in these amounts in the compositions of this invention. In particular the compound of formula I where $R^1$ is a hydrogen atom and $R^2$ is $H_9C_4O$— or tert.butyl; or wherein $R^1$ and $R^2$ are both 2-ethylhexoxy.

Compositions of this invention are useful as cosmetic light-screening compositions, comprising cosmetically acceptable carrier containing at least one fatty phase. Preferably the cosmetic light-screening composition contains 4-tert.butyl-4'-methoxydibenzoylmethane.

As described above, the UV-B filter agent(s) of the cosmetic light-screening composition may at least be one of the group consisting of cinnamates, salicylates, benzophenones, diphenylacrylates, camphor derivates, polymeric materials and microfine pigments preferably at least one of the group consisting of nanopigment metallic oxides of cerium, iron, titanium, zinc or zirconium, especially of titanium or zinc, and polymers with hydrocarbon structure or siloxane structure carrying at least one ultraviolet-light-absorbing group. The cosmetic light screening composition is useful for protecting human skin or human hair against ultraviolet radiation.

Accordingly this invention includes a method of protecting skin or hair against UV radiation which comprises applying to the skin or hair the composition of claim 1. This composition contains an effective amount of compounds which absorb UV radiation, thus when applied to such body surfaces, will prevent UV radiation from reaching them. The exact amount and frequency of application will depend on such factors as the condition, exposure, and activity of the individual using the composition. However, the individual will readily determine how much and how often to apply the compound to avoid sunburn, for example.

The compositions of this invention also may contain standard cosmetic ingredients. A cosmetically acceptable carrier preferably contains at least one fatty phase since both components of the composition of this invention i.e. of the light-screening agent(s) and the photostabilizing compound of formula I, are lipophilic. The cosmetic formulations contain thus at least one fatty phase, and the formulations can consequently present themselves in the form of emulsions, lotions or gels.

Suitably the cosmetic screening composition takes the form of an oil, a lotion, a gel, a solid stick, an emulsion, e.g. cream, milk or of a vesicular dispersion of ionic or nonionic amphiphilic lipids, an aerosol, a spray, a foam, a powder, a shampoo, a hair conditioner or lacquer or a make-up or the like. In case a cosmetic composition for the protection of human hair the suitable formulations are shampoos, conditioners, lotions, gels, emulsions, dispersions, lacquers or the like. The preparation of all these formulations is well known to the skilled artisan.

The usual solvents known to the skilled practitioner can be used for the preparation of these forms, e.g. oils, waxes, alcohols, polyols. The preferred agents are fatty acids, esters, fatty alcohols, but also ethanol, isopropanol, propylene glycol, glycerine or the like are useful. The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments or the like.

The most important advantage of the novel photostabilizer stems from the fact that the artisan skilled in the art is completely free in the choice regarding the material used for the filtration of the UV-B radiation as already said above.

Compounds of formula I are prepared by process analogous to those known from the literature (G. Charles, Bull. Soc. Chim. Fr., 1559 (1962); P. L. Pickard and T. L. Tolbert, J. Org. Chem., 26, 4886 (1961)).

The following examples explain the invention in more detail, and are not intended to limit it in any way.

EXAMPLE 1

General Procedure

Ketimine preparation

A Grignard-nitrile complex was prepared by the dropwise addition of 40 mmoles of nitrile to a stirred Grignard reagent prepared from 45 mmoles of halide and 46 mmoles of magnesium turning in 25 ml of anhydrous ether, followed by 4 hrs reflux. After cooling to room temperature, the stirred complex was decomposed by the dropwise addition of 270 mmoles of anhydrous methanol. The suspension was filtered and the filtrate was concentrated to give the desired ketimine.

Compounds of formula I

Compounds of formula I were prepared by mixing 40 mmoles of the adequate ketimine with 40 mmoles of malonitrile at room temperature. Compounds of formula I were purified by chromatography. They are listed in table 1.

TABLE 1

| Compounds | Structure | 1 max (nm) EtOH | $E^{1\%}cm$ | mp ° C. |
|---|---|---|---|---|
| 1 | NC–C(CN)=C(phenyl)(4-BuO-phenyl) | 358 | 605 | 80–82 |
| 2 | NC–C(CN)=C(4-$H_{17}C_8O$-phenyl)(4-$OC_8H_{17}$-phenyl) | 344 | 520 | 53–55 |
| 3 | NC–C(CN)=C(phenyl)(4-tert-butyl-phenyl) | 330 | 561 | 86–88 |

EXAMPLE 2

In this example, photostability experiments according to the protocol described in International Journal of Cosmetic Science 18, 167–177 (1996) were performed.

The desired stabilisation of the material of UV-A filters is easily established by strict parallel experiments with the respective UV-A filter and the stabiliser using an appropriately equipped Xenon lamp as a solar simulator. Irradiated are standard preparations of the investigated products, e.g. solutions in, preferably, higher boiling cosmetic solvents, e.g. isopropyl myristate, the resulting solution being spread on glass plates. After irradiation, the plates are immersed into a suitable solvent (e.g. in ethanol) and analysed by HPLC. The stabilising effect is directly correlated to the difference of recovered amount of UV-A filter from non-irradiated and irradiated samples. (The presence of any UV-B filter is simulated by inserting a Mylar®: D50 sheet between the light source and the samples; see International Journal of Cosmetic science 18, 167–177 (1996), page 173).

The following table shows the stabilising effect expressed as percentage with respect to non exposed sample.

Mixtures containing Parsol 1789 and compounds of formula I were irradiated in parallel with 3 controls (Parsol 1789 without stabilizer; Parsol 1789 with Benzophenone-4 (a UV-A filter); Parsol 1789 with octocrylene (a known UV-B stabilizer), for comparison purposes. Table 2 and FIG. 1 show the results obtained using 1% of compounds according to the invention.

Figure 2:
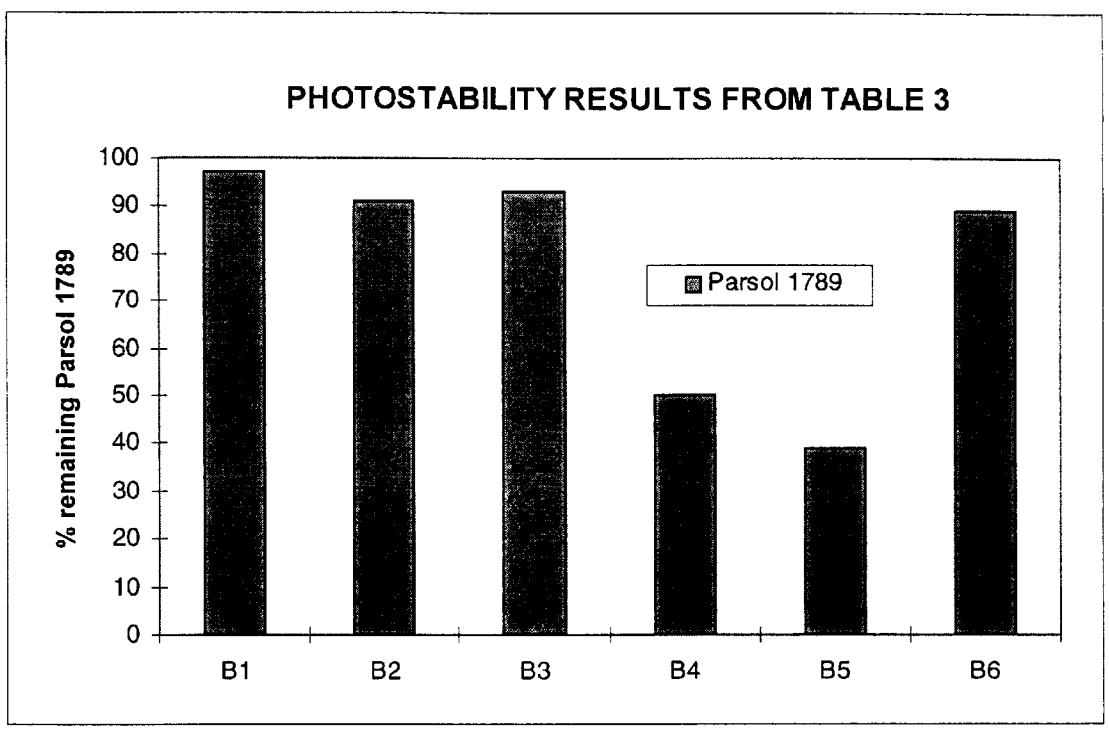
Figure 3:
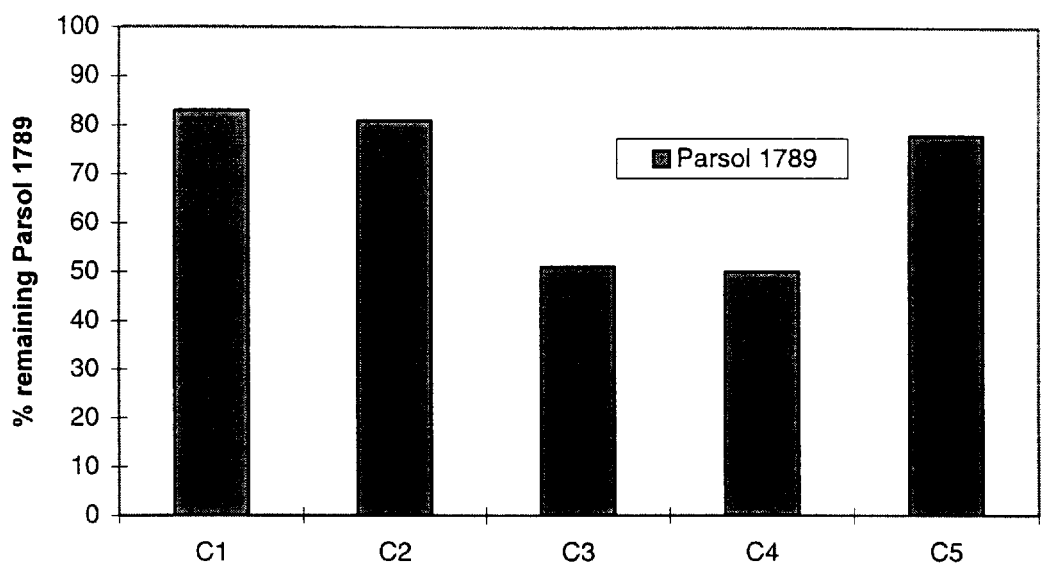

Table 3 and FIG. 2 show the results obtained using 2% of compounds according to the invention.

TABLE 2

| Entry | Composition (% in weight) | Remaining amount of Parsol 1789 in % after irradiation |
|---|---|---|
| A1 (invention) | 2% Parsol 1789<br>1% Compound 1 from table 1 | 88% |
| A2 (invention) | 2% Parsol 1789<br>1% Compound 2 from table 1 | 83% |
| A3 (invention) | 2% Parsol 1789<br>1% Compound 3 from table 1 | 90% |
| A4 (comparative) | 2% Parsol 1789 | 50% |
| A5 (comparative) | 2% Parsol 1789<br>1% Benzophenone-4 | 48% |
| A6 (comparative) | 2% Parsol 1789<br>1% octocrylene | 84% |

TABLE 3

| Entry | Composition (% in weight) | Remaining amount of Parsol 1789 in % after irradiation |
|---|---|---|
| B1 (invention) | 2% Parsol 1789<br>2% Compound 1 from table 1 | 97% |
| B2 (invention) | 2% Parsol 1789<br>2% Compound 2 from table 1 | 91% |
| B3 (invention) | 2% Parsol 1789<br>2% Compound 3 from table 1 | 93% |
| B4 (comparative) | 2% Parsol 1789 | 50% |
| B5 (comparative) | 2% Parsol 1789<br>2% Benzophenone-4 | 39% |
| B6 (comparative) | 2% Parsol 1789<br>2% octocrylene | 89% |

These results clearly show the remarkable photostabilisation effect of Parsol 1789 brought by the compounds of formula I (invention) (A1–A3 compared to A4 and B1–B3 compared to B4). These results are as good as those obtained with octocrylene (a known UV-B photostabiliser see EP-A-780119) while UV-A filter like Benzophenone-4 was not efficient. No loss of stabilizer was observed.

EXAMPLE 3

Photostability experiments of emulsions containing Parsol 1789, compounds of formula I, Octocrylene and Benzophenone-4 were performed. Emulsions were spread on glass plates and irradiated using a Xenon lamp as solar simulator (UV-B+UV-A light). After irradiation, the plates were immersed into a suitable solvent (e.g. in ethanol) and analysed by HPLC. The stabilising effect is directly correlated to the difference of recovered amount of UV-A filter from non-irradiated and irradiated samples.

TABLE 4

Oil in water emulsion

| | Ingredients % w/w | C1 | C2 | C3 | C4 | C5 |
|---|---|---|---|---|---|---|
| A | Butyl Methoxydibenzoylmethane (Parsol 1789) | 2 | 2 | 2 | 2 | 2 |
| | compound 1 from table 1 | 1 | | | | |
| | compound 2 from table 1 | | 1.5 | | | |
| | Benzophenone-4 | | | | 3 | |
| | Octocrylene | | | | | 1 |
| | Glyceryl mono myristate | 4 | 4 | 4 | 4 | 4 |
| | PVP-Eicosen Copolymer | 2 | 2 | 2 | 2 | 2 |
| | Cetylalcohol | 2 | 2 | 2 | 2 | 2 |
| | Caprilic capric triglyceride | 10 | 10 | 10 | 10 | 10 |
| | Butylhydroxytoluene | 0.1 | 0.1 | 0.1 | 0.1 | 0.1 |
| | Phenoxyethanol & Methylparaben & Ethylparaben & Propylparaben & Butylparaben | 0.6 | 0.6 | 0.6 | 0.6 | 0.6 |
| | Amphisol K | 2 | 2 | 2 | 2 | 2 |
| B | Propylene Glycol | 10 | 10 | 10 | 10 | 10 |
| | Disodium EDTA | 0.1 | 0.1 | 0.1 | 0.1 | 0.1 |
| | Carbomer 981 | 10 | 10 | 10 | 10 | 10 |
| | Demineralised water qsp | 100 | 100 | 100 | 100 | 100 |

Mix part A and B separately at 85° C. Combine A and B under stirring. Finally, correct pH to 7 with potassium hydroxide 10%.

TABLE 5

| Entry | UV-filter composition (% in weight) | Remaining amount of Parsol 1789 in % after irradiation |
| --- | --- | --- |
| C1 (invention) | 2% Parsol 1789 1% compound 1 of Tab. 1 | 83% |
| C2 (invention) | 2% Parsol 1789 1.5% compound 2 of Tab. 1 | 81% |
| C3 (comparative) | 2% Parsol 1789 — | 51% |
| C4 (comparative) | 2% Parsol 1789 3% Benzophenone-4 | 50% |
| C5 (comparative) | 2% Parsol 1789 1% octocrylene. | 78% |

These results clearly show the remarkable photostabilisation effect of Parsol 1789 brought by the compound of formula 1 (invention), (C1–C2 compared to C3). These results are as good as those obtained with octocrylene, a known UV-B photostabilizer, while UV-A filter like Benzophenone-4 was not efficient. No loss of stabiliser was observed.

We claim:

1. A composition which comprises a dibenzoylmethane capable of absorbing UV-A radiation and a compound of formula I

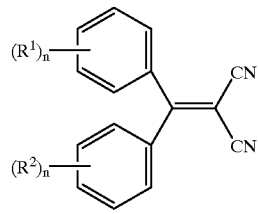

wherein $R^1$ and $R^2$ are independently hydrogen, alkyl or alkoxy containing 1 to 18 carbon atoms provided that $R^1$ and $R^2$ are not both hydrogen; and n is 1 or 2 in an amount effective to photostabilize the dibenzolymethane, and a cosmetically acceptable carrier.

2. A composition of claim 1 which comprises about 0.1 to about 5.0% by weight of the compound of formula I.

3. A composition of claim 2 which comprises about 0.5 to about 2.0% by weight of the compound of formula I.

4. A composition of claim 1 wherein either or both rings of the dibenzoylmethane are substituted with one or more lower alkyl or lower alkoxy groups.

5. A composition of claim 4 wherein the dibenzoylmethane is substituted at one or more of positions 2, 4, 5, 6, and 4'.

6. A composition of claim 4 wherein wherein either or both rings of the dibenzoylmethane are substituted with one or more of methyl, tert-butyl, isopropyl, or methoxy.

7. A composition of claim 6 wherein the dibenzoylmethane is selected from the group consisting of 2-methyldibenzoylmethane, 4-methyl-dibenzoylmethane, 4-tert-butyldibenzoyl-methane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane.

8. A composition of claim 7 wherein the dibenzoylmethane is 4-tert-butyl-4'-methoxydibenzoylmethane.

9. A composition of claim 1 which also comprises a compound capable of absorbing UV-B radiation.

10. A composition of claim 9 wherein the compound capable of absorbing UV-B radiation is selected from the group consisting of cinnamates, salicylates, benzophenones, diphenylacrylates, camphor derivates, polymeric materials and microfine pigments having a particle size in the nano- and/or low micrometer region.

11. A composition of claim 10 wherein the compound capable of absorbing UV-B radiation is selected from the group consisting of pigment metallic oxides of cerium, iron, titanium, zinc or zirconium, especially of titanium or zinc, and polymers with hydrocarbon structure or siloxane structure carrying at least one ultraviolet-light-absorbing group.

12. A composition of claim 1 wherein n is 1 and $R^1$ is hydrogen.

13. A composition of claim 12 wherein $R^2$ is in the para position.

14. A composition of claim 1 wherein n is 1 and $R^1$ and $R^2$ are independently alkyl or alkoxy containing 3 to 12 carbon atoms.

15. A composition of claim 13 wherein either or both of $R^1$ and $R^2$ are in the para position.

16. A composition of claim 14 wherein $R^2$ is alkyl or alkoxy containing 3 to 12 carbon atoms.

17. A composition of claim 16 wherein $R^2$ is alkoxy containing 3 to 12 carbon atoms.

18. A composition of claim 16 wherein $R^2$ is alkyl containing 3 to 12 carbon atoms.

19. A composition of claim 18 wherein $R^2$ is tert.butyl, propyl, isopropyl, n-butyl, pentyl, or hexyl.

20. A composition of claim 19 wherein $R^2$ is in the para position.

21. A compound of claim 19 wherein $R^2$ is tert.butyl.

22. A composition of claim 16 wherein $R^2$ is n-propoxy-, isopropoxy-, n-butoxy-, 1-methyl propoxy-, 2-methylpropoxy-, n-pentoxy-, 1,1-dimethylpropoxy-, 3-methylbutoxy-, hexoxy-, 2,2-dimethylpropoxy-, heptoxy-, 1-methyl-1-ethylpropoxy-, 2-ethylhexoxy- or octoxy.

23. A composition of claim 22 wherein $R^2$ is in the para position.

24. A composition of claim 22 wherein $R^2$ is n-butoxy.

25. A composition of claim 14 wherein $R^1$ and $R^2$ are selected from the group consisting of n-propoxy-, isopropoxy-, n-butoxy-, 1-methyl propoxy-, 2-methylpropoxy-, n-pentoxy-, 1,1-dimethylpropoxy-, 3-methylbutoxy-, hexoxy-, 2,2-dimethylpropoxy-, heptoxy-, 1-methyl-1-ethylpropoxy-, 2-ethylhexoxy- and octoxy.

26. A compound of claim 25 wherein $R^1$ and $R^2$ are in the para position.

27. A compound of claim 26 wherein $R^1$ and $R^2$ are 2-ethylhexoxy.

28. A composition of claim 21 wherein the dibenzoyl-methane is 4-tert-butyl-4'-methoxydibenzoylmethane.

29. A compound of claim 28 which additionally comprises a compound capable of absorbing UV-B radiation.

30. A composition of claim 28 which comprises about 0.1 to about 5.0% by weight of the compound of formula I.

31. A composition of claim 30 which comprises about 0.5 to about 2.0% by weight of the compound of formula I.

32. A composition of claim 24 wherein the dibenzoyl-methane is 4-tert-butyl-4'-methoxydibenzoylmethane.

33. A compound of claim 32 which additionally comprises a compound capable of absorbing UV-B radiation.

34. A composition of claim 32 which comprises about 0.1 to about 5.0% by weight of the compound of formula I.

35. A composition of claim 34 which comprises about 0.5 to about 2.0% by weight of the compound of formula I.

36. A composition of claim 26 wherein the dibenzoylmethane is 4-tert-butyl-4'-methoxydibenzoylmethane.

37. A compound of claim 36 which additionally comprises a compound capable of absorbing UV-B radiation.

38. A composition of claim 36 which comprises about 0.1 to about 5.0% by weight of the compound of formula I.

39. A composition of claim 38 which comprises about 0.1 to about 5.0% by weight of the compound of formula I.

40. A method of protecting skin or hair against UV radiation which comprises applying to the skin or hair the composition of claim 1.

* * * * *